(12) United States Patent
Müller et al.

(10) Patent No.: US 8,514,423 B2
(45) Date of Patent: Aug. 20, 2013

(54) DEVICE FOR IMAGING A FLAT OBJECT AND PRINTING MATERIAL PROCESSING MACHINE HAVING THE DEVICE

(75) Inventors: Tobias Müller, Hirschberg (DE); Andreas Rupprecht, Mauer (DE)

(73) Assignee: Heidelberger Druckmaschinen Aktiengesellschaft, Heidelberg (DE)

( * ) Notice: Subject to any disclaimer, the term of this patent is extended or adjusted under 35 U.S.C. 154(b) by 588 days.

(21) Appl. No.: 12/727,505

(22) Filed: Mar. 19, 2010

(65) Prior Publication Data

US 2010/0245882 A1   Sep. 30, 2010

(30) Foreign Application Priority Data

Mar. 26, 2009   (DE) .......................... 10 2009 015 266

(51) Int. Cl.
| | |
|---|---|
| *H04N 1/04* | (2006.01) |
| *H04N 1/46* | (2006.01) |
| *H04N 3/06* | (2006.01) |
| *H04N 5/225* | (2006.01) |
| *H04N 5/228* | (2006.01) |
| *H04N 9/04* | (2006.01) |

(52) U.S. Cl.
USPC .......... 358/1.14; 358/474; 358/482; 358/483; 358/505; 358/506; 358/514; 348/202; 348/207.2; 348/208.14; 348/210.99

(58) Field of Classification Search
None
See application file for complete search history.

(56) References Cited

U.S. PATENT DOCUMENTS

| | | | |
|---|---|---|---|
| 5,010,241 | A | 4/1991 | Butterworth |
| 5,526,458 | A | 6/1996 | Hochgraf |

(Continued)

FOREIGN PATENT DOCUMENTS

| | | |
|---|---|---|
| DE | 43 04 815 A1 | 8/1994 |
| DE | 689 26 664 T2 | 10/1996 |
| EP | 0 377 973 A2 | 7/1990 |
| WO | 2007/035472 A2 | 3/2007 |

OTHER PUBLICATIONS

German Patent and Trademark Office Search Report, dated Nov. 10, 2009.

*Primary Examiner* — Benny Q Tieu
*Assistant Examiner* — Haris Sabah
(74) *Attorney, Agent, or Firm* — Laurence A. Greenberg; Werner H. Stemer; Ralph E. Locher

(57) ABSTRACT

A device for imaging a flat object, for example a paper sheet in a printing machine, includes a light source, preferably an LED row, a lens and an image sensor. An observation angle between the object plane and lens axis is flat, that is to say less than 45°. The light source illuminates the flat object in a first, near region with light of a first wavelength and illuminates the flat object in a second, far region with light of a second wavelength. The first wavelength is shorter than the second wavelength, preferably being blue and red spectral regions. The first region is disposed nearer the image sensor than the second region. The device permits the so-called chromatic aberration of the lens to be utilized to advantageously reduce the tilt angle of the image sensor required by the so-called Scheimpflug condition. A printing machine having the device is also provided.

14 Claims, 1 Drawing Sheet

(56) References Cited

U.S. PATENT DOCUMENTS

| | | |
|---|---|---|
| 6,313,913 B1 | 11/2001 | Nakagawa et al. |
| 6,654,173 B1 * | 11/2003 | Uozu et al. .................... 359/619 |
| 2001/0050765 A1 * | 12/2001 | Antonelli et al. ................ 356/71 |
| 2003/0210433 A1 * | 11/2003 | Westcott et al. ............... 358/474 |
| 2004/0196519 A1 * | 10/2004 | Kikuchi ........................ 359/204 |
| 2007/0057164 A1 | 3/2007 | Vaughnn et al. |
| 2007/0097386 A1 * | 5/2007 | Tregoning et al. ............. 358/1.6 |

* cited by examiner

DEVICE FOR IMAGING A FLAT OBJECT AND PRINTING MATERIAL PROCESSING MACHINE HAVING THE DEVICE

CROSS-REFERENCE TO RELATED APPLICATION

This application claims the priority, under 35 U.S.C. §119, of German Patent Application DE 10 2009 015 266.0, filed Mar. 26, 2009; the prior application is herewith incorporated by reference in its entirety.

BACKGROUND OF THE INVENTION

Field of the Invention

The present invention relates to a device having a light source, a lens and an image sensor, for imaging a flat object. The present invention also relates to a printing material processing machine having the device.

In printing material processing machines such as, for example, printing machines, it is necessary to monitor the transport of the flat substrates, sheets or webs. It is normal to make use of sensors or cameras for that purpose that also enable monitoring at poorly accessible points. However, narrow construction spaces frequently only permit the sensors and/or cameras to be disposed at the side of the transport path in such a way that imaging and consequently monitoring, are only possible at a flat angle.

As is illustrated in FIG. 1 and explained in the associated description of the figure, sharp imaging of near and far zones when recording pictures of flat objects at small or flat observation angles is possible only by observing the so-called Scheimpflug condition. Consequently, in accordance with the Scheimpflug condition, large tilt angles of the image sensors result and therefore a poor light yield often results as well.

U.S. Pat. No. 5,526,458 teaches a light guiding element in a Scheimpflug configuration that includes an array of tightly packed optical fibers for guiding light. The element has parallel entry and exit surfaces, between which the fibers run on a curved path. Incident light therefore leaves the element at a changed angle and strikes a downstream detector perpendicularly. However, that technical solution to the problem requires acceptance of light loses as a result of the restricted numerical aperture of the tilted fiber entry surfaces.

International Publication No. WO 2007/035472 A2, corresponding to U.S. Patent Application Publication No. US 2007/0057164, shows a technical solution to the problem in which optically denser prisms are used to shorten parts of the beam path when imaging inclined objects.

German Translation DE 689 26 664 T2 of European Patent EP 0 377 973 B1, corresponding to U.S. Pat. No. 5,010,241, describes a detector configuration and illumination system for a barcode scanner with a large depth of focus. An illumination device 113 generates light in a narrow frequency range and is disposed, for the purpose of projecting a light layer along a first Scheimpflug plane, with reference to a focusing device 119 in order to illuminate a strip.

German Published, Non-Prosecuted Patent Application DE 43 04 815 A1 discloses an optical sensor for measuring object-height profiles with a light source composed of a multiplicity of light points disposed in a plane, for example a row of light emitting diodes, which can also have different wavelengths. The imaging of the reflected light takes place under observance of the so-called Scheimpflug condition.

SUMMARY OF THE INVENTION

It is accordingly an object of the invention to provide a device for imaging a flat object and a printing material processing machine having the device, which overcome the hereinafore-mentioned disadvantages of the heretofore-known devices and machines of this general type and which enable a good light yield of a sensor and therefore a high sensitivity to be achieved by satisfying the Scheimpflug condition.

With the foregoing and other objects in view there is provided, in accordance with the invention, a device for imaging a flat object, for example a printed material sheet, comprising a light source, a lens and an image sensor. An (observation) angle between the object plane and the lens axis is flat, that is to say less than 45°. The light source illuminates the flat object in a first region with light of a first wavelength and the light source illuminates the flat object in a second region with light of a second wavelength. The first wavelength is shorter than the second wavelength and the first region is disposed nearer the image sensor than the second region.

By satisfying the Scheimpflug condition, the device according to the invention advantageously enables a good light yield of the sensor, and therefore a high sensitivity, to be achieved. The inventive use of two mutually different wavelengths advantageously permits the so-called chromatic aberration of the lens to be utilized to advantageously reduce the tilt angle of the image sensor required by the Scheimpflug condition, with the sensitivity of the image sensor thereby being improved.

In accordance with another feature of the invention, that is advantageous with regard to generation of different wavelengths and is therefore preferred, the light source has at least two luminous elements.

In accordance with a further feature of the invention, with regard to the generation of a multiplicity of mutually different wavelengths, that is advantageous and therefore preferred, the light source has a one dimensional row or a two dimensional array of luminous elements.

In accordance with an added feature of the invention, which is advantageous for the energy efficient and cost effective generation of substantially monochromatic light in each case and is therefore preferred, the luminous elements are constructed as light-emitting diodes.

In accordance with an additional feature of the invention, which is advantageous and therefore preferred, a first luminous element generates light substantially in the blue spectral region, and a second luminous element generates light substantially in the red spectral region. Since, due to the chromatic aberration of the lens, blue and red light leads to image points as far as possible in front of, or as far as possible behind the image plane tilted according to Scheimpflug, it is possible to reach a maximum reduction in the tilt angle using these different wavelengths of the limits of the visible spectrum. Moreover, it is also possible to operate using ultraviolet and infrared light if the image sensor is constructed for the purpose of detecting the same.

In accordance with yet another feature of the invention, that is advantageous for imaging large area objects, for example large print formats, and is therefore preferred, the light source has three or more luminous elements and generates a quasi-continuous wavelength profile.

In accordance with yet a further feature of the invention, which is advantageous and therefore preferred, the light source is disposed above the flat object and the image sensor is disposed next to the flat object.

In accordance with yet an added feature of the invention, that is advantageous and therefore preferred, the (tilt) angle between the image sensor and the lens plane is less than approximately 30° or less than approximately 20°.

With the objects of the invention in view, there is also provided a printing material processing machine, for example a printing machine, in particular a sheet-processing rotary printing machine for lithographic offset printing or, for example, a postpress machine, comprising at least one device described as above with reference to the invention.

In accordance with a concomitant feature of the printing material processing machine of the invention, that is advantageous given restricted construction spaces and is therefore preferred, a camera of the device, including the lens and the image sensor, is disposed substantially at the side next to a printing material transport path.

Other features which are considered as characteristic for the invention are set forth in the appended claims, noting that the described invention and the described, advantageous developments of the invention also constitute advantageous developments of the invention in combination with one another, for example, a preferred embodiment of the inventive device can include all of the features of several of the claims, such as by using an array instead of a row of luminous elements.

Although the invention is illustrated and described herein as embodied in a device for imaging a flat object and a printing material processing machine having the device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
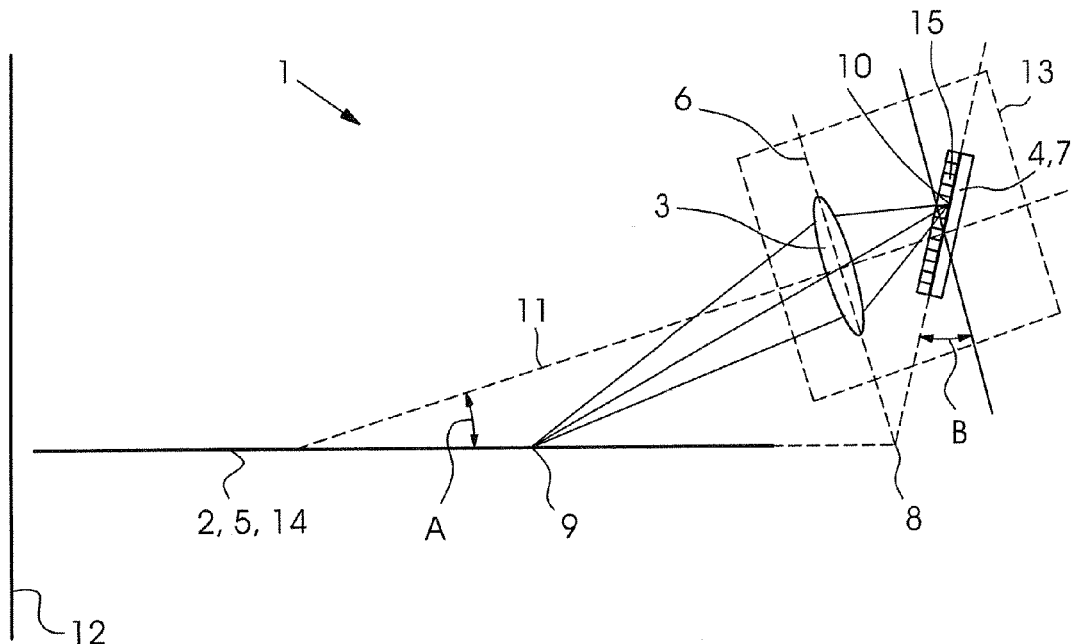
FIG. 1 is a diagrammatic, longitudinal-sectional view of a device for imaging a flat object.

Referring now in detail to the figures of the drawings, in which mutually corresponding elements are provided with the same reference symbols, and first, particularly, to FIG. 1 thereof, there is seen a device 1 for imaging a flat object 2, having a lens (or objective) 3 and an image sensor 4. In accordance with the so-called Scheimpflug condition, an object plane 5, a lens or object plane 6 and an image plane 7 must intersect on a line of intersection 8 so that each object point 9 of the object plane 5 is imaged by the lens 3, assumed to be ideal, at a sharp image point 10 of the image plane 7. In the real case, an object point 9 may not lie too far removed from a central axis 11 of the lens 3, in order to avoid undesired, intolerable aberrations.

A consideration of an angle A (referred to below as an observation angle) between the object plane 5 and the lens axis 11, an angle B (referred to below as a tilt angle) between the image sensor 4 and the lens plane 6 as well as their dependence on one another yields, from the Scheimpflug condition that is to be satisfied, that the tilt angle B increases with a decreasing observation angle A. In this case, the tilt angle B can assume values from approximately 45° up to over approximately 80°.

If the aim is to image flat objects 2, for example printing materials such as paper, cardboard or foil in the form of sheets or webs, in machines 12, for example printing or postpress machines, the possibilities of placing a device 1 for imaging are often constrained by narrow construction spaces, and it is therefore actually often necessary to place the device 1 for imaging at a flat or even very flat observation angle A.

Mention may be made herein, as an example, of the monitoring of a sheet path at inaccessible points, or points that cannot be inspected with the usual measures, in printing machines 12. A camera 13, including the lens or objective 3 and the image sensor 4, is therefore disposed at the side of a sheet transport path 14 and at a flat observation angle A in order to be able to detect the sheet 2 and/or its sheet surface, since sufficient free construction space is not available over the transport path 14.

However, conventional CCD or CMOS image sensors 4 do not allow a very large tilt angle B, for example greater than approximately 20° to approximately 30°, since the light yield or sensitivity decreases with an increasing tilt angle B, particularly if the image sensor 4 is equipped with a so-called microlens array 15. This can result in insufficiently focused images.

Figure 2:
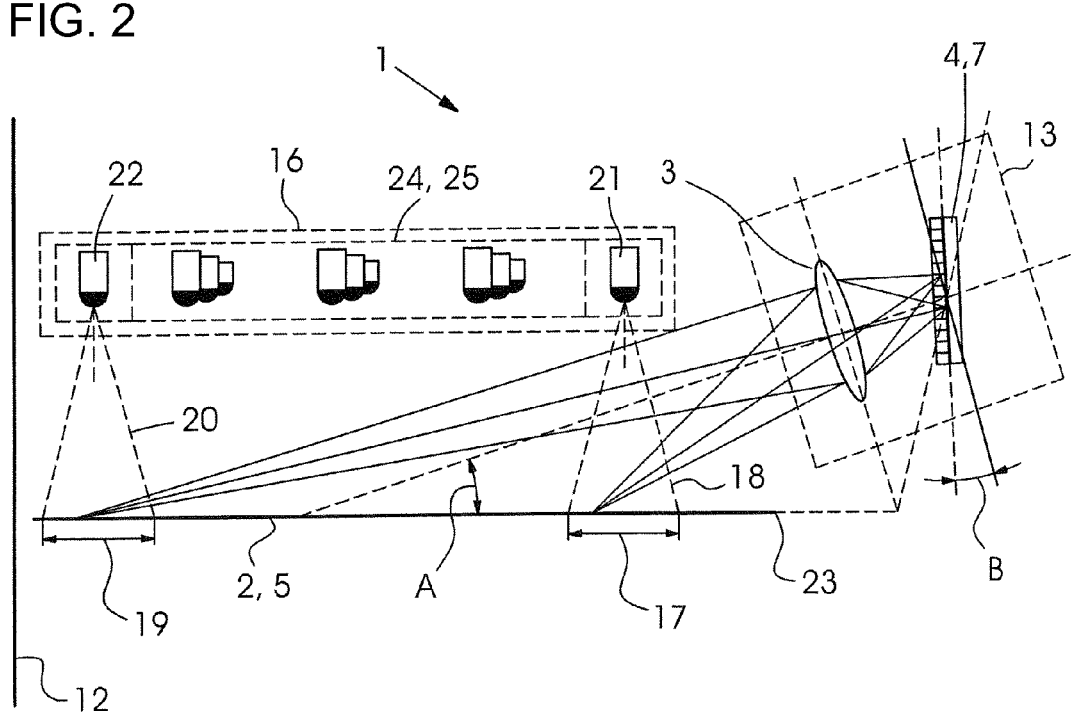
FIG. 2 is a longitudinal-sectional view of an exemplary embodiment of a device for imaging a flat object according to the invention.

FIG. 2 shows a preferred embodiment of a device 1 according to the invention for imaging a flat object 2, having a light source 16, a lens (or objective) 3 and an image sensor 4, with a flat observation angle A of less than 45° being provided.

According to the invention, the light source 16 illuminates the flat object 2 in a first region 17 with light 18 of a first wavelength, and in a second region 19, different from the first region 17, with light 20 of a second wavelength. The light source 16 can be provided with at least two luminous elements 21 and 22, preferably light-emitting diodes (LEDs, which generate approximately monochromatic light) for this purpose. The luminous elements 21 and 22 can be disposed over the object plane 5 and illuminate the flat object 2 from above.

According to the invention, the first wavelength is shorter than the second wavelength. For example, a blue or near ultraviolet LED (approximately 380 to approximately 470 nanometer wavelength) can be provided as the first luminous element 21, and a red or near infrared LED (approximately 630 to approximately 850 nanometer wavelength) can be provided as the second luminous element 22. Lasers or laser diodes can also be used for illumination as an alternative.

According to the invention, the first region 17 is disposed nearer the image sensor 4 or the camera 13 (near zone) than the second region 19 (far zone), as is to be seen from FIG. 2. This means, in the case of a lateral configuration of the lens and image sensor, or of the camera 13, with reference to the flat object 2 or to its side edge 23, that the first region 17 is disposed nearer the side edge 23 than the second region 19. The side edge in this case is that edge of the flat object which lies parallel to its transport direction.

The invention utilizes the otherwise disturbing influence of the so-called chromatic aberration, specifically that lenses 3 have a focal length dependent on the wavelength, meaning that light 18 of shorter wavelength is focused onto a point in front of the image plane 7, which is tilted (in accordance with Scheimpflug), whereas light 20 of longer wavelength is focused onto a point behind the image plane 7, which is tilted (in accordance with Scheimpflug). Consequently, according to the invention, the tilt angle B can advantageously be selected to be smaller than is required solely by the Scheimpflug condition, and the light yield can be improved.

In addition, the invention enables the use of lenses or objectives 3 that are simple and uncorrected with regard to the disturbances by the chromatic aberration instead of corrected, so-called achromatic objectives.

A one-dimensional row 24 or a two-dimensional array 25 of luminous elements, for example LEDs, can also be used within the meaning of the invention as the light source 16, with more than two (three, four, five, six, seven, eight, nine, ten or more) mutually different wavelengths being generated to illuminate the flat object 2. The use of more than two wavelengths can advantageously be used for the purpose of generating a quasicontinuous wavelength change, and thus to simulate a continuous wavelength change along the observation direction.

The CCD or CMOS sensors that can be used as the image sensor 4 have relatively small dimensions, for example approximately 11 millimeters diagonally, and the lenses 3 which are used preferably have relatively small focal lengths. The optical system therefore has a relatively large depth of focus. Consequently, the image quality itself is even good enough whenever, in accordance with the invention, use is made of two wavelengths instead of the ideally continuous wavelength profile.

The invention claimed is:

1. A device for imaging a flat object, the device comprising:
   a lens having a lens axis enclosing a flat angle of less than 45° with an object plane of the flat object;
   a light source illuminating the flat object in a first region with light of a first wavelength and illuminating the flat object in a second region with light of a second wavelength;
   a single image sensor upon which the light of the first wavelength and the light of the second wavelength impinge;
   the first wavelength being shorter than the second wavelength; and
   the first region being nearer said single image sensor than the second region.

2. The device according to claim 1, wherein said light source has at least two luminous elements.

3. The device according to claim 2, wherein said at least two luminous elements of said light source are more than two luminous elements disposed in a row or an array.

4. The device according to claim 2, wherein said luminous elements are light-emitting diodes.

5. The device according to claim 2, wherein said luminous elements include a first luminous element generating light substantially in blue spectral region and a second luminous element generating light substantially in red spectral region.

6. The device according to claim 3, wherein said luminous elements are light-emitting diodes.

7. The device according to claim 3, wherein said luminous elements include a first luminous element generating light substantially in blue spectral region and a second luminous element generating light substantially in red spectral region.

8. The device according to claim 1, wherein said light source has three or more luminous elements and generates a quasicontinuous wavelength profile.

9. The device according to claim 1, wherein said light source is disposed above the flat object, and said single image sensor is disposed next to the flat object.

10. The device according to claim 1, wherein said lens defines a lens plane enclosing an angle with said single image sensor of less than approximately 30°.

11. The device according to claim 1, wherein said lens defines a lens plane enclosing an angle with said single image sensor of less than approximately 20°.

12. A printing material processing machine, comprising:
    at least one device according to claim 1.

13. The printing material processing machine according to claim 12, wherein the printing material processing machine is selected from group consisting of a printing machine, a sheet-processing rotary printing machine for lithographic offset printing and a postpress machine.

14. The printing material processing machine according to claim 12, which further comprises a printing material transport path, and a camera disposed substantially at a side next to said printing material transport path, said camera include said lens and said single image sensor.

* * * * *